US009456898B2

(12) United States Patent
Barnes et al.

(10) Patent No.: US 9,456,898 B2
(45) Date of Patent: Oct. 4, 2016

(54) HEART VALVE PROSTHESIS WITH OPEN STENT

(71) Applicant: Abiomed, Inc., Danvers, MA (US)

(72) Inventors: Terrence Gerard Barnes, Lowell, MA (US); Scott Corbett, Beverly, MA (US)

(73) Assignee: ABIOMED, INC., Danvers, MA (US)

( * ) Notice: Subject to any disclaimer, the term of this patent is extended or adjusted under 35 U.S.C. 154(b) by 17 days.

(21) Appl. No.: 14/367,718

(22) PCT Filed: Dec. 21, 2012

(86) PCT No.: PCT/US2012/071403
§ 371 (c)(1),
(2) Date: Jun. 20, 2014

(87) PCT Pub. No.: WO2013/096854
PCT Pub. Date: Jun. 27, 2013

(65) Prior Publication Data
US 2015/0112421 A1    Apr. 23, 2015

Related U.S. Application Data

(60) Provisional application No. 61/579,958, filed on Dec. 23, 2011.

(51) Int. Cl.
*A61F 2/24*       (2006.01)
*A61F 2/89*       (2013.01)

(52) U.S. Cl.
CPC .......... *A61F 2/2427* (2013.01); *A61F 2/2403* (2013.01); *A61F 2/2412* (2013.01); *A61F 2/2418* (2013.01); *A61F 2/89* (2013.01)

(58) Field of Classification Search
CPC ....... A61F 2/24; A61F 2/2427; A61F 2/2428
USPC .................................................. 623/2.1–2.19
See application file for complete search history.

(56) References Cited

U.S. PATENT DOCUMENTS

| 5,562,729 A | 10/1996 | Purdy et al. |
| 7,329,278 B2 * | 2/2008 | Seguin .................. A61F 2/2418 623/2.1 |

(Continued)

FOREIGN PATENT DOCUMENTS

| AU | 2002212418 B2 | 3/2006 |
| DE | 102009037739 A1 | 12/2010 |

(Continued)

OTHER PUBLICATIONS

Edwards, Transcatheter Heart Valves, accessible via URL: http://www.edwards.com/eu/products/transcathetervalves/Pages/thvhome.aspx (accessed Mar. 31, 2016).

(Continued)

*Primary Examiner* — Suzette J Gherbi
(74) *Attorney, Agent, or Firm* — Ropes & Gray LLP

(57) ABSTRACT

A prosthetic apparatus is disclosed including: a tubular stent disposed about a longitudinal axis and extending from a proximal end to a distal end, the stent defining a tubular passage between the ends. The tubular stent has a proximal portion, a distal portion, and a middle portion located between the proximal and distal portions. The proximal and distal portions each comprise a mesh of support struts forming at least one ring of open elements disposed about the longitudinal axis. The middle portion features open regions which reduce or eliminate blockage of sensitive anatomical features at an implantation site.

31 Claims, 12 Drawing Sheets

(56) References Cited

U.S. PATENT DOCUMENTS

| | | | | |
|---|---|---|---|---|
| 7,758,632 B2* | 7/2010 | Hojeibane | ............ | A61F 2/2412 623/1.13 |
| 8,048,153 B2* | 11/2011 | Salahieh | ............... | A61F 2/2418 623/2.11 |
| 8,540,768 B2* | 9/2013 | Stacchino | ............. | A61F 2/2418 623/2.1 |
| 8,795,356 B2* | 8/2014 | Quadri | ................. | A61F 2/2418 623/2.11 |
| 8,801,779 B2* | 8/2014 | Seguin | ................. | A61F 2/2418 623/2.1 |
| 8,920,492 B2* | 12/2014 | Stacchino | ............. | A61F 2/2418 606/108 |
| 8,986,329 B2* | 3/2015 | Seguin | ................. | A61F 2/2409 606/151 |
| 8,998,979 B2* | 4/2015 | Seguin | ................. | A61F 2/2409 623/2.1 |
| 9,023,100 B2* | 5/2015 | Quadri | ................. | A61F 2/2418 623/2.11 |
| 9,060,856 B2* | 6/2015 | Seguin | ................. | A61F 2/2409 |
| 9,149,357 B2* | 10/2015 | Seguin | ................. | A61F 2/2403 |
| 2004/0093060 A1* | 5/2004 | Seguin | ................. | A61F 2/2418 623/1.11 |
| 2005/0234546 A1 | 10/2005 | Nugent et al. | | |
| 2006/0122693 A1 | 6/2006 | Biadillah et al. | | |
| 2009/0164006 A1* | 6/2009 | Seguin | ................. | A61F 2/2418 623/2.38 |
| 2009/0222082 A1 | 9/2009 | Lock et al. | | |
| 2009/0287299 A1 | 11/2009 | Tabor et al. | | |
| 2010/0168839 A1 | 7/2010 | Braido et al. | | |
| 2010/0185277 A1* | 7/2010 | Braido | .................. | A61F 2/2412 623/2.18 |
| 2010/0249911 A1* | 9/2010 | Alkhatib | ............... | A61F 2/2418 623/1.26 |
| 2011/0098800 A1* | 4/2011 | Braido | .................. | A61F 2/2412 623/1.16 |
| 2011/0213461 A1* | 9/2011 | Seguin | .................. | A61F 2/2418 623/2.18 |
| 2011/0218619 A1* | 9/2011 | Benichou | ............... | A61F 2/2412 623/2.11 |
| 2011/0257739 A1 | 10/2011 | Corbett | | |
| 2012/0101567 A1 | 4/2012 | Jansen | | |

FOREIGN PATENT DOCUMENTS

| | | |
|---|---|---|
| EP | 1690515 A1 | 8/2006 |
| WO | WO-2007/081820 A1 | 7/2007 |

OTHER PUBLICATIONS

CoreValve TAVR Platform—Transcatheter Aortic Valve Replacement, accessible via URL: http://www.corevalve.com/us/product/index.htm (accessed Mar. 31, 2016).

* cited by examiner

| Sample Name | Leaflet Thickness (in.) | Pressure Drop (mmHg) @ Various Flow Rates | | | | |
|---|---|---|---|---|---|---|
| | | 5 L/min | 10 L/min | 15 L/min | 20 L/min | 24 L/min |
| Crown 1 | 0.0105 | 7.3 | 9.7 | 14.5 | 19.5 | 25.2 |
| Crown 2 | 0.0085 | 6.5 | 9.8 | 13.2 | 17.8 | 22.7 |
| Crown 3 | 0.0066 | 6.0 | 9.3 | 14.8 | 19.8 | 25.2 |

Fig. 9

In Vitro Backflow Leakage Rate

| Sample Name | Avg. Leaflet Thickness (in.) | Leakage Rate (mL/sec) |
|---|---|---|
| Crown 1 | 0.0105 | 7.1 |
| Crown 2 | 0.0085 | 3.6 |
| Crown 3 | 0.0066 | 7.9 |

Fig. 10

HEART VALVE PROSTHESIS WITH OPEN STENT

RELATED APPLICATIONS

This application is the U.S. National Stage of International Application Number PCT/US2012/071403, filed Dec. 21, 2012, which claims priority to U.S. Provisional Patent Application No. 61/579,958, filed Dec. 23, 2011. The entire contents of the foregoing applications are hereby incorporated herein by reference.

BACKGROUND

Prosthetic heart valves are used to replace damaged or diseased heart valves. Prosthetic heart valves for human patients have been available since the 1950s. Today, there are three general types of prosthetic heart valves, including mechanical valves, tissue valves, and polymer valves. In some cases, a heart valve prosthesis is implanted into an annular opening in a patient's heart following surgical removal of a diseased or damaged natural valve. The valve can be secured in the annulus of the opening through the use of sutures or pins that penetrate the host tissue and an outside edge of the valve. Alternatively, the valve can be secured in the annulus by suturing the host tissue to a sewing ring. Heart valves function essentially as one-way check valves for blood flow through the beating heart.

The term "mechanical valve" refers to mono- or multi-leaflet (typically bi-leaflet) heart valves having a valve orifice fabricated at least in part of a rigid, biologically compatible material such as pyrolytic carbon, and comprising essentially no biological components. The term "bio-prosthetic valve" refers to a multi-leaflet (e.g., bi-leaflet or tri-leaflet) heart valve having at least some biological components such as tissue or tissue components. The biological components of tissue valves are obtained from a donor animal (typically bovine or porcine), and the valve may comprise either biological materials alone or biological materials with man-made supports or stents. The term "polymeric valve" refers to a multi-leaflet (e.g., tri-leaflet or bi-leaflet) heart valve having at least some elastomeric polymer components, including at least elastomeric polymer valve leaflets.

A tri-leaflet heart valve prosthesis typically includes an annular valve body and three flexible leaflets attached thereto. The valve body includes an annular base and three leaflet support posts located at the circumference of the annulus. In some cases, a sewing ring annularly coupled to the periphery of the valve body may provide a place for sutures to be applied when the valve is implanted. The leaflets are attached to the three shaped posts along an attachment curve, and they also each have a free, unattached edge remote from the attachment curve. The place where two adjacent leaflets come together at one of the support posts is called the commissure, and the generally curved area on the leaflet between the free edge and the attachment curve is known as the belly of the leaflet. The free edges of the three leaflets come together at a "triple point" generally on the axis of the valve.

When blood flows in the forward direction, the energy of the blood flow deflects the three leaflets away from the center of the annulus and allows blood to flow through. When blood flows in the reverse direction, the three leaflets engage each other in a coaptive region, occlude the valve body annulus and prevent the flow of blood.

Heart valves may be may be implanted through open heart surgical procedures. More recently, heart valves have been developed that are implanted percutaneously, e.g., using transcatheter procedures. Transcatheter percutaneous aortic replacement valve devices typically include a valve body mounted on a tubular expandable (e.g. balloon expandable or self-expanding) stent or frame. Examples include the SAPIEN device available from Edwards Lifesciences of Irvine, Calif. or the CoreValve device available from Medtronic of Minneapolis, Minn.

Percutaneously implanted devices obviate the need for major open surgical procedures. However, implantation of these devices may be difficult. Replacement valves are typically sensitive devices, and care must be taken to avoid damage during implantation. In the case of aortic replacement valves, further difficulties may arise from the particular anatomy of the aortic region. The aortic region is characterized by high blood pressure subjecting tissue is in the area to high physical strains. Supporting stents for aortic replacement valves therefore must sufficiently be robust and rigid to operate in this environment. However, the introduction of such a stent in the region raises the risk that other vessels, such as the coronary arteries ostium dextra and ostium sinistra (referred to herein as the coronary ostia) descending on both sides of the aorta, may be disrupted in their function.

SUMMARY

The inventors have realized that a percutaneously implantable aortic replacement valve device may be provided featuring, e.g., a polymeric tri-leaflet valve mounted in an expandable stent. As detailed herein, the stent may include one or more open regions adjacent the valve at positions corresponding to the coronary ostia. This allows the device to be implanted more easily, and reduces the risk of damaging, blocking, or otherwise disrupting the function of the ostia lowers the incidence of unwanted effects such as stenosis. Further, in cases where the device is an expandable device, positioning of the open regions adjacent the leaflets of the valve allows the device to be crimped down to a small size without damaging the sensitive valve leaflets.

The inventors have realized that a multi-leaflet polymeric heart valve (e.g. a tri-leaflet valve) may be mounted on the stent. In some embodiments, the valve features a partially open leaflet position which reduces forward flow pressure loss. In some embodiments, the valve features flexible valve posts with tips made of a soft flexible material. The flexibility of the posts allows the leaflets to properly close to block reverse blood flow without experiencing excessive stress or strain. These features act synergistically to provide a valve with advantageous durability, forward flow pressure loss and efficiency characteristics.

In one aspect, a prosthetic apparatus is disclosed including: a tubular stent disposed about a longitudinal axis and extending from a proximal end to a distal end, the stent defining a tubular passage between the ends. In some embodiments, the tubular stent has a proximal portion, a distal portion, and a middle portion located between the proximal and distal portions. In some embodiments, the proximal and distal portions each include a mesh of support struts forming at least one ring of open elements disposed about the longitudinal axis. In some embodiments, the middle portion includes: a plurality of elongated posts extending along a direction substantially parallel the longitudinal axis between the proximal and distal portions; and a crown shaped mounting ring attached to the posts and configured to mount a polymeric valve within the tubular passage; and a plurality of open regions. In some embodiments, the crown shaped ring may, additionally, or alternatively, be attached to the proximal portion of the stent.

In some embodiments, the open elements are open diamond shaped elements.

In some embodiments, the plurality of open regions each define an open area along the outer surface of the tubular support that is at least about 20 times the area of each of the open elements.

In some embodiments, the plurality of open regions each define an open area along the outer surface of the tubular support that is at least about 40 times the area of each of the open elements.

In some embodiments, the proximal and distal portions include a ring of N open elements, the plurality of stent posts consist of M posts extending between the rings, and the ratio of N to M is at least 4 to 1, at least 5 to 1, or is at least 6 to 1. In some embodiments, N=15 and M=3.

Some embodiments include a tubular polymeric sheath extending along the outer surface of the tubular support member from the proximal portion to the distal portion, but does not substantially cover the open regions in the middle portion. In some embodiments, the sheath encapsulates the elongated posts.

In some embodiments, the sheath includes regions of reinforced thickness corresponding to the elongated posts.

In some embodiments, the sheath includes regions of reinforced thickness corresponding to one or more of the support struts or the mounting ring.

Some embodiments include one or more sutures securing the sleeve to the stent.

Some embodiments include the polymeric heart valve. In some embodiments, the valve includes: a valve body having a central axis extending along the direction of the longitudinal axis of the tubular stent and having a body fluid pathway extending along the central axis from an inflow end to an outflow end; a flexible outer support disposed about an outer circumference of the body and including at least three flexible valve posts each extending in the axial direction to a tip and each attached to at least one of the elongated posts; and at least three flexible leaflets extending from the crown shaped mounting ring, each of the leaflets having an attached edge defining an attachment curve along the mounting ring extending between a respective pair of flexible valve posts, and where pairs of leaflets define a respective commissure at each of the at least three flexible valve posts; where the crown shape ring includes a plurality of points each corresponding to a flexible valve post and attached to a respective one of the elongated posts of the stent.

In some embodiments, the flexible outer support of the valve encapsulates a portion of the tubular stent. In some embodiments, the stents posts extend through the flexible outer support, e.g., extending through the valve posts.

In some embodiments, the at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end, and in the closed position, each of the flexible valve posts flexes inward toward the central axis.

In some embodiments, the tip of each valve post is formed of a material having a flexibility greater than the remainder of the valve post In some embodiments, the stent is configured to be crimped to reduce the outer diameter of the stent from an uncrimped diameter to a crimped diameter without damaging the valve. In some embodiments, the uncrimped diameter is at least about 20 mm and the crimped diameter is less than about 6 mm.

In some embodiments, the tubular stent includes a shape memory material. In some embodiments, the shape memory material includes Nitinol.

In some embodiments, stent is a self expanding stent.

In some embodiments, the stent is configured such that, when implanted in the human heart such that the valve is positioned proximal the location of the native aortic valve, the open regions are positioned proximal to the coronary ostia.

In some embodiments, the apparatus consists essentially of biocompatible materials.

In another embodiment, a method is disclosed including: obtaining the apparatus of any of the types described above; and percutaneously implanting the apparatus in a human subject such that that the valve is positioned proximal the location of the native aortic valve, the open regions are positioned proximal to the coronary ostia.

In some embodiments, the step of percutaneously implanting the apparatus includes: crimping the stent; using an introducer to position the stent in a desired location; and removing the introducer and expanding the stent to an uncrimped state.

In some embodiments, expanding the stent to an uncrimped state includes allowing the stent to self expand.

In another aspect, a method of making prosthetic apparatus is disclosed including: obtaining a tubular stent of any of the types described above; placing the stent on a mandrel; forming a polymeric valve mounted on the mounting ring by a process including dip molding; forming a tubular polymeric sheath extending along the outer surface of the tubular support member from the proximal portion to the distal portion, but does not substantially cover the open regions in the middle portion.

In some embodiments, the step of forming the tubular polymeric sheath includes a thermoforming process including: applying a polymer material to the outer surface of the tubular stent; disposing a heat shrink tube about the polymer material and the stent; applying heat to soften the polymer material and cause the heat shrink tube to shrink and apply force to mold the polymer material to form the sheath.

In some embodiments, forming the sheath includes encapsulating one or more of the support struts and the elongated posts Some embodiments include, during the thermoforming process, applying an air flow to valve to avoid thermal damage to the valve.

Some embodiments include applying strips of polymer material to reinforce the sheath at locations corresponding to the elongated posts or the mounting ring.

Some embodiments include applying additional polymer material to reinforce the sheath at locations corresponding to the struts.

Various embodiments may include any of the above-described features, alone, or in any suitable combination.

BRIEF DESCRIPTION OF THE DRAWINGS

FIG. 9 is a table showing forward pressure loss as a function of flow rate for embodiments of a valve with various leaflet thicknesses mounted on a stent featuring a crown shaped mounting ring of the type shown in FIGS. 2A-2C.

FIG. 10 is a table showing backflow leakage for embodiments of a valve with various leaflet thicknesses mounted on a stent featuring a crown shaped mounting ring of the type shown in FIGS. 2A-2C.

DETAILED DESCRIPTION

Generally, the present technology relates to a percutaneously implantable device that includes a polymeric heart valve. The device includes openings that prevent blockage or damage of anatomical features at the implantation site.

Figure 1:
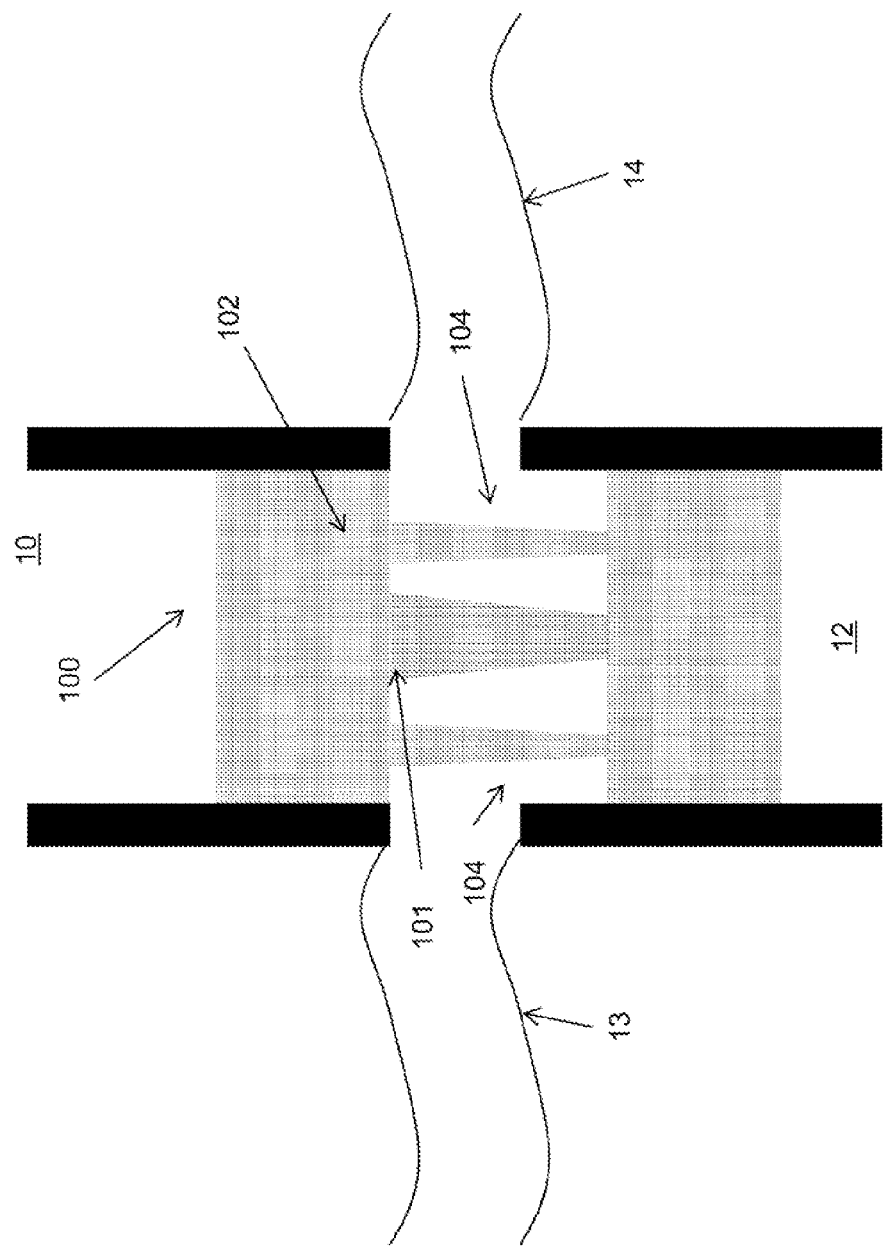
FIG. 1 illustrates a prosthetic aortic valve replacement device in the aortic region following implantation.

For example, FIG. 1 shows a prosthetic aortic valve replacement device 100 in the aortic region following implantation. The device lies between the heart 10 and the aorta 12 at about the position the aortic valve would normally be located. As detailed below, the device 100 includes a polymeric valve 101 mounted in a tubular stent 102. The left and right coronary vessels 13/14 or 14/13, depending on whether the depicted view is from above or from below are also shown. The tubular stent includes openings 104 positioned such that the coronary vessels 13, 14 are not blocked or occluded.

Figure 2A:
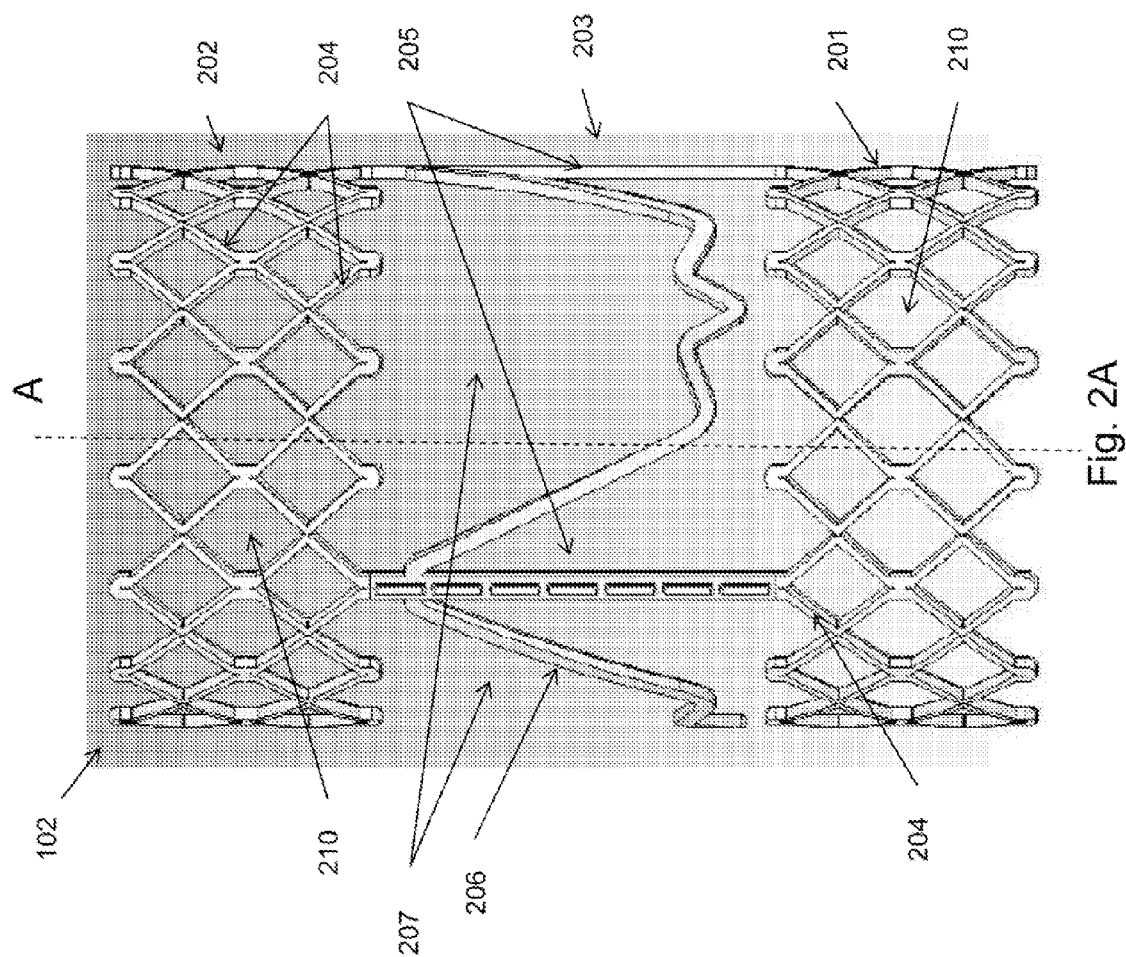
FIG. 2A shows a perspective view of a tubular stent. For clarity, only one half of the tubular stent is shown. The remaining half of the stent may be obtained by reflection in a plane that slices through the tubular stent and includes the longitudinal axis A
Figure 2B:
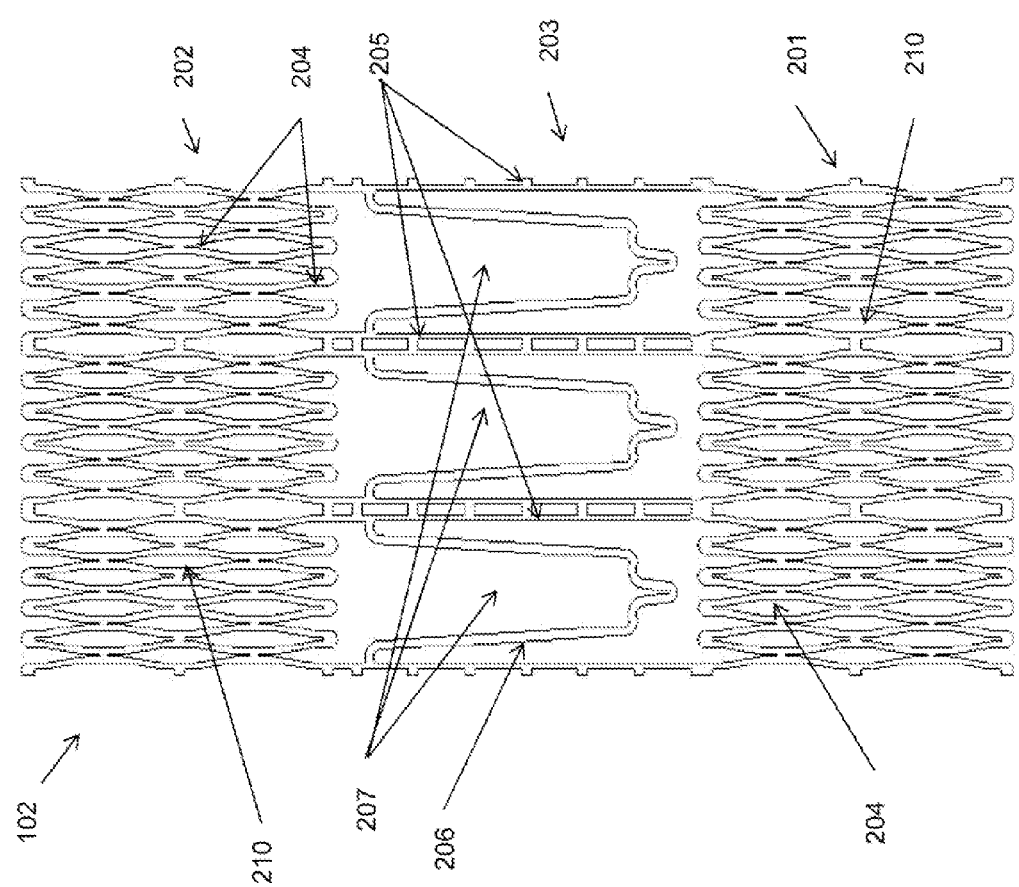
FIG. 2B shows a view of the tubular stent of FIG. 2A having been cut along its length and laid flat.
Figure 2C:
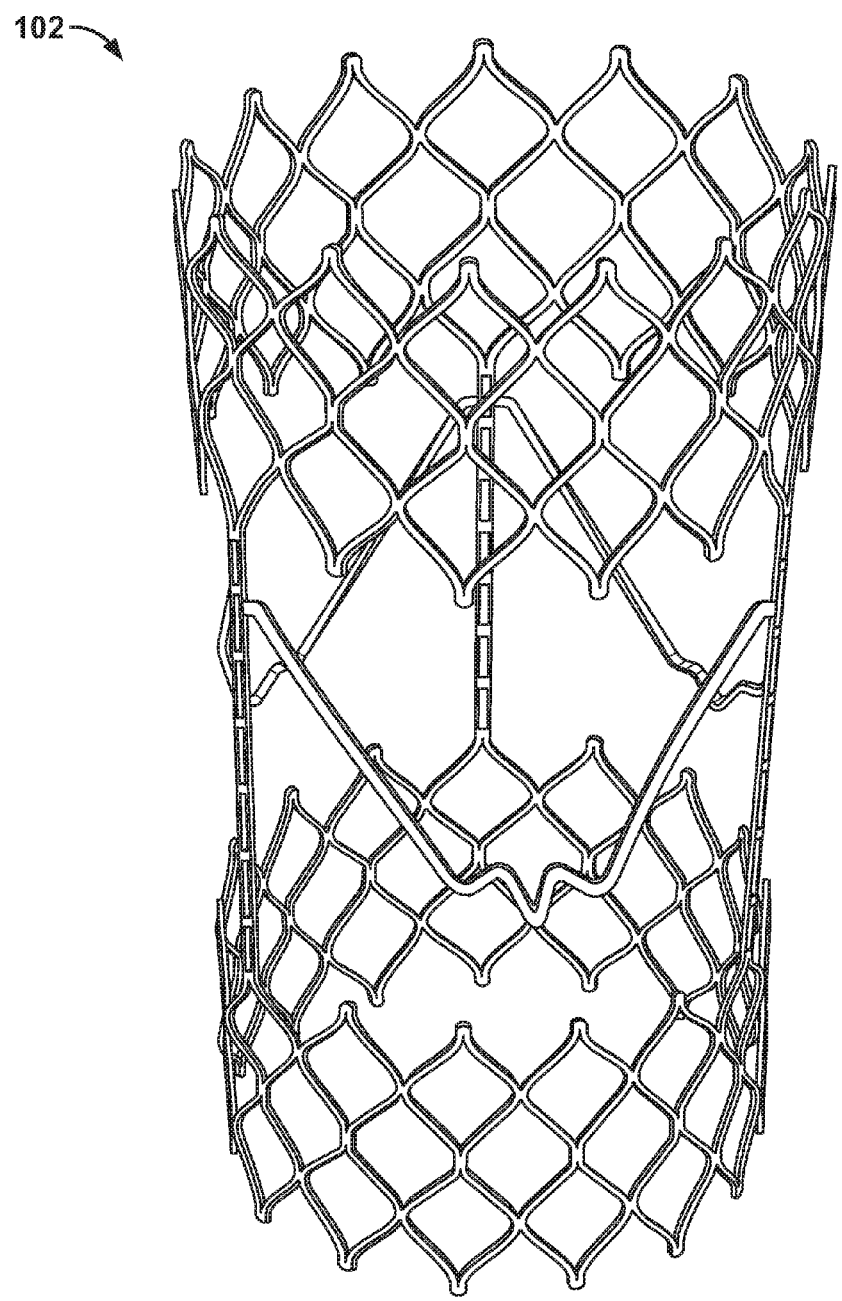
FIG. 2C is a photograph of a stent of the type illustrated in FIGS. 2A and 2B.

FIGS. 2A, 2B and 2C show views of the tubular stent 102. FIG. 2A shows a perspective view. FIG. 2B shows a view of the tubular sent sliced along its length and rolled out flat. FIG. 2C is a photograph of an embodiment of the tubular stent 102.

Referring to FIGS. 2A-2C, the tubular stent 102 is disposed about a longitudinal axis A. The stent 102 extends from proximal end (towards the bottom of the figures) to a distal end (towards the top of the figures) and defines a tubular passage between the two ends. The valve 101 (not shown) is mounted on the stent 102 in the tubular passage transverse to the axis A.

The stent 102 has a proximal portion 201, a distal portion 202 and a middle potion 203. The middle portion 203 is located between the proximal and distal portions 201, 202. The proximal and distal portions each include a mesh of support struts 204. The support struts are arranged to form rings of open elements 210 (as shown, diamond elements) disposed about the axis A.

The middle portion 203 includes elongated posts 205 that extend along a direction substantially parallel to the axis A, connecting the proximal portion 201 to the distal portion 202. A mounting element for mounting the valve is attached to the posts 205. As shown, the mounting element is a crown shaped mounting ring 206 suitable for mounting a trileaflet polymeric valve of the type described in greater detail below. The points of the crown shaped mounting ring 206 are attached to the posts 205. In some embodiments, the crown shaped mounting ring 206 may, additionally or alternatively, be attached to the proximal portion 201 of the stent 102. For example, for the embodiment shown, an attachment may be made between the proximal pointing features on the ring 206 between the posts 205.

As shown the crown shaped mounting ring 206 includes three points extending towards the distal end of the stent 102. However, in other embodiments, any other number of points may be used, e.g., 1, 2, 3, 4, 5, etc. In some embodiments, the mounting element may have any other suitable shape, e.g. a circle, an oval, a ring with sinusoidal undulations towards and away from the distal end of the stent 102, a ring with sawtooth undulations towards and away from the distal end of the stent 102, etc.

The middle portion 203 also includes open regions 207 located distal the mounting ring 206 that are completely free of posts, struts, or any other structures. These open regions 207 correspond to the openings 104 described with reference to FIG. 1.

In typical embodiments, the area of each of the open regions 207 will be larger than the area of the open elements 210 that form the mesh found in the proximal and distal portions. For example, in various embodiments, the area of each of the open regions 207 may be at least 2, 3, 4, 5, 10, 20, 30, 40, 50, 60, 70, 80, 90, 100 or more times the area of each of the open elements 210. For example, in some embodiments, the area of each of the open regions 207 may be in the range of 2-100 times the area of the area of the open elements 210, or any subrange thereof. As shown, the ratio of areas is about 50. For example, in one embodiment, the area of the open region 207 is about 300 mm$^2$, while the area of the open diamond elements 210 is about 6 mm$^2$.

Accordingly, the relatively fine mesh of support struts 204 forming the rings of open elements 210 in the proximal and distal portions 201, 202 provide good mechanical support for the valve 101 and stent 102. Meanwhile, the larger open regions 207 in the middle portion 203 ensure that the portion of the device 100 located near the coronary ostia is free or substantially free from any obstructions (e.g., as shown in FIG. 1).

As shown, the proximal and distal portions 201 and 202 each include three rings of open diamond shaped elements 210 formed from the support struts 204. In other embodiments, more or fewer rings may be used, e.g., 1, 2, 3, 4, 5, or more rings. In various embodiments the elements 210 may have other shapes including rectangular, square, polygonal, round, oval, etc. In some embodiments the struts 204 may form a mesh with an irregular or random pattern.

The number of posts 205 may also be chosen to ensure that the middle portion 203 remains suitably free of obstructions. In some embodiments, no more than, e.g., 6, 5, 4, 3, 2, or 1 posts may be used. In general, the number of posts 205 may be fewer than the number of open elements 210 found in each ring of elements in the proximal and distal portions 201 and 202. For example, in some embodiments there are N open elements 210 in each ring, and M posts 205, where M and N are integers. In some embodiments, the ratio of N to M is at least 2 to 1, 3 to 1, 4 to 1, 5 to 1 (as shown), 6 to 1, 7 to 1, 8 to 1, 9 to 1, 10 to 1 or more. For example, in the embodiment shown, the proximal and distal portions 201 and 202 each contain three rings of open diamond elements 210, with each ring having fifteen elements 210, therefore N=15. This embodiments has three posts 205, therefore M=3, giving a ration of N to M of 5 to 1.

The support struts 204 and posts 205 of the stent 102 may be made from any suitable material. In some embodiments, a shape memory material is used, e.g. a nickel titanium allow such as the material marketed under the trade name Nitinol. In various embodiments, other materials may be used, alone or in any suitable combination, including metallic, plastic, polymer, or other materials. In various embodiments, the materials may be biocompatible.

Figure 3:
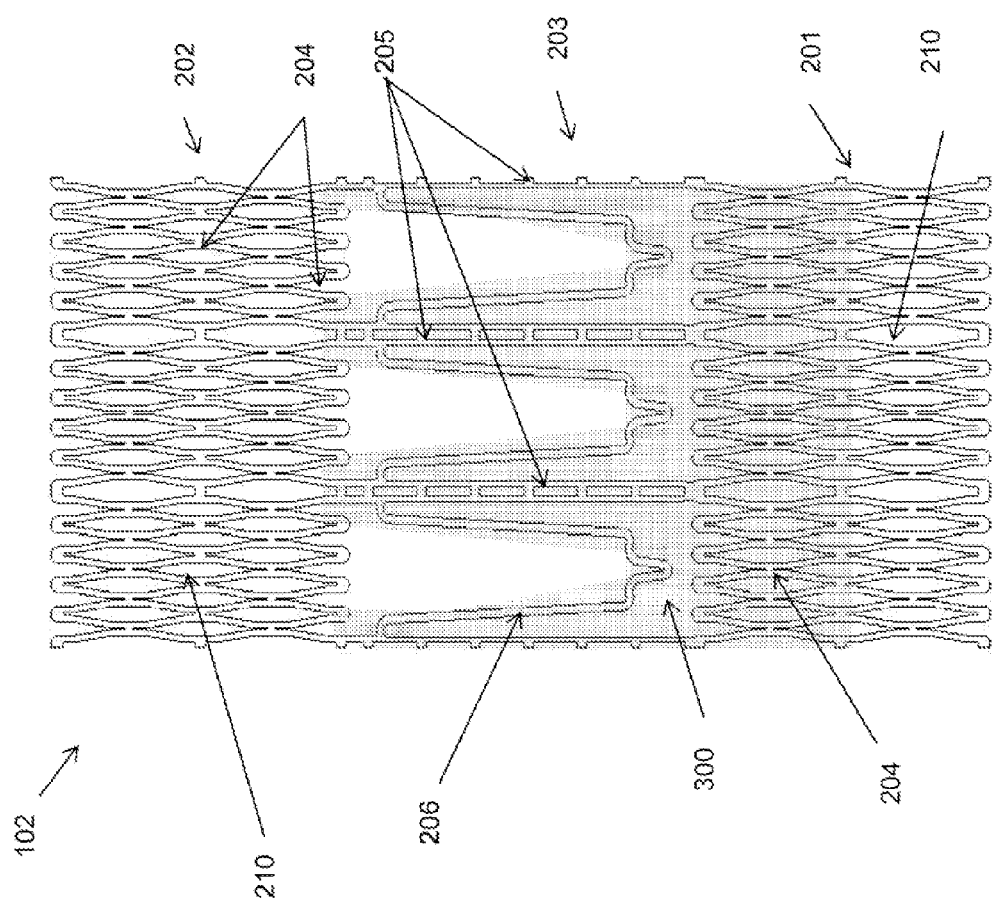
FIG. 3 shows a stent of FIGS. 2A-C in same view found in FIG. 2B, further including a sheath on the stent. The sheath is indicated by the gray area.

Referring to FIG. 3, in some embodiments, a sheath 300 is formed that extends along the outer surface of the stent 102 from the proximal portion 201 to the distal portion 202, without substantially covering the open regions 207 of the middle portion 203. The sheath 300 may encapsulate the elongated posts 205 and some or all of the support struts 204 of the proximal and/or distal portions 201, 202 of the stent 102.

The sheath may be made of any suitable material, e.g., a polymer material such as silicone, polyurethane, polyether ether ketone (PEEK), etc. In some embodiments, the polymer material may be the material produced under the trade name Angioflex by Abiomed, Inc. of Danvers, Mass. In some embodiments, the sheath 300 includes regions of reinforced thickness at locations corresponding to the elongated posts 205 or the support struts 204. In some embodiments, the sheath 300 may be secured to the stent 102 using one or more sutures.

Figure 4:
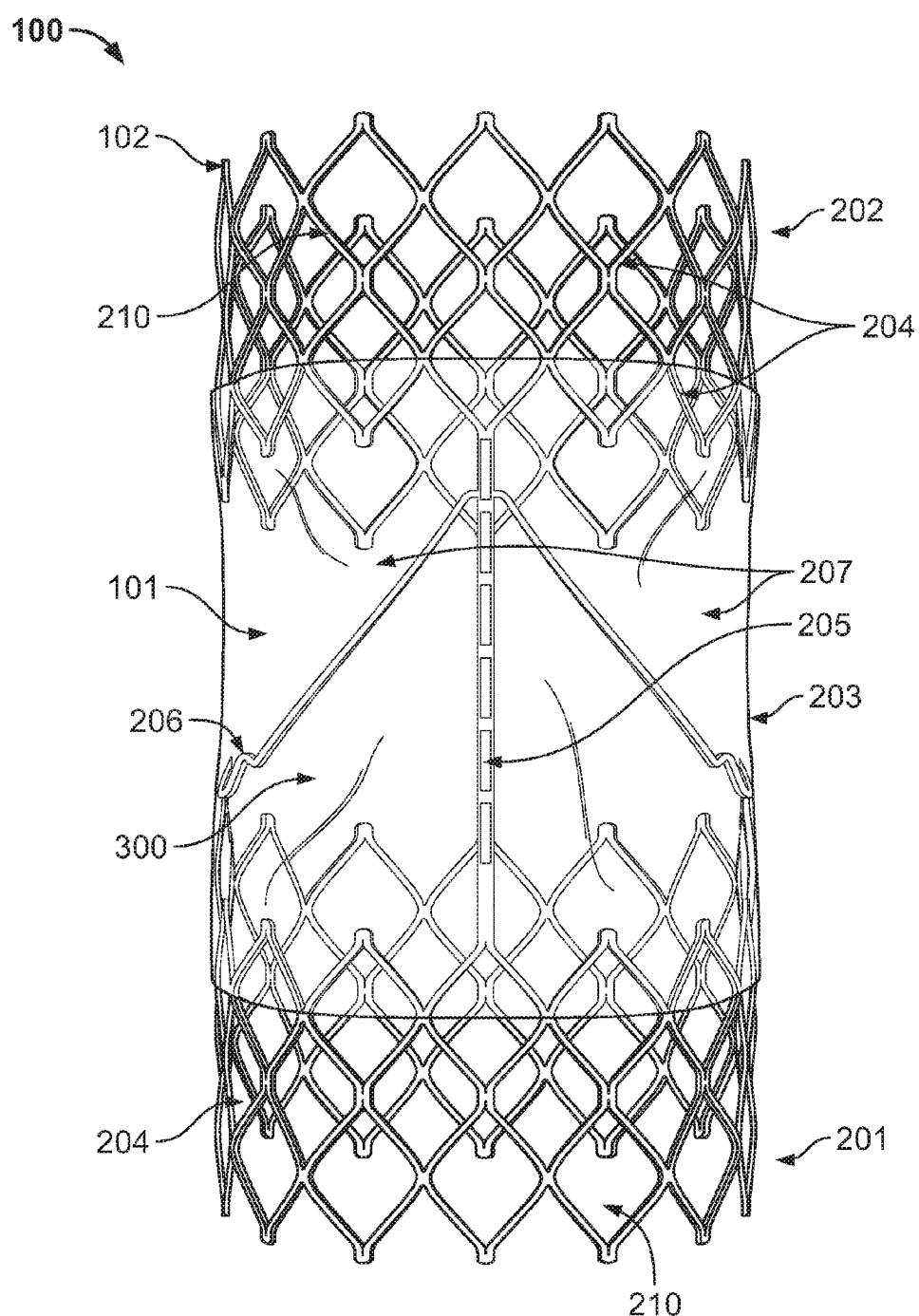
FIG. 4 is a photograph of a prosthetic aortic valve replacement device including the stent shown in FIG. 2C with a polymeric sheath and valve attached.

As shown in FIG. 4, in some embodiments, a polymeric trileaflet valve 101 is mounted on the crown shaped mounting ring 206. In some embodiments the valve may be of the type described in the Valve Application, incorporated by reference above. The sheath 300 may connect to an outer circumference of the body of the valve 101.

Figure 5:
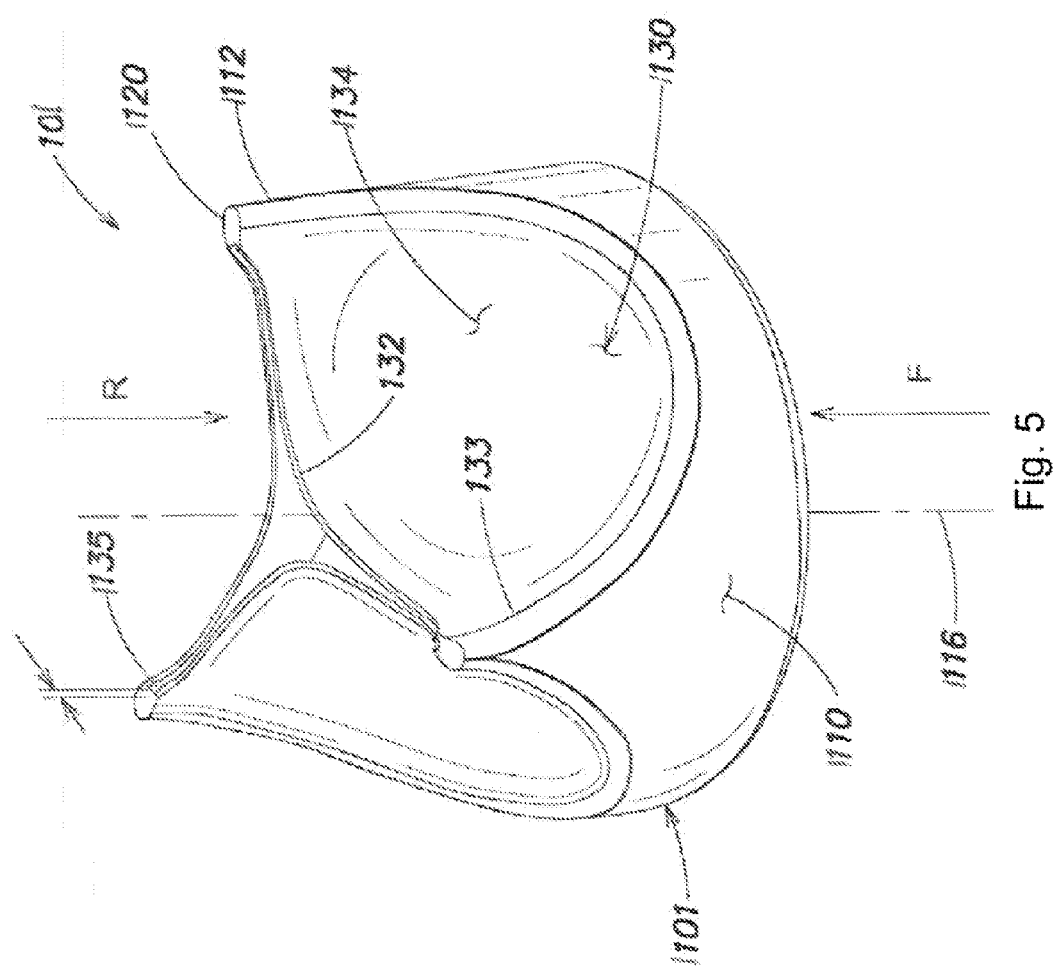
FIG. 5 is a detailed illustration of the valve of the prosthetic aortic valve replacement device shown in FIG. 4.

FIG. 5 shows a detailed view of the valve 101. The valve 101 includes an annular, generally cylindrical elastomeric valve body 1101 disposed about a central axis 1116, and having a sealable fluid passageway extending axially from an inflow end (as shown, the bottom) to an outflow end (as shown, the top). The valve 101 includes a flexible outer portion 1110 connected to the mounting ring 206 (not shown) and having at least three flexible valve posts 1112 each of which extends axially to a valve post tip 1120. As discussed in greater detail below, valve post tip 1120 may be made of a material having greater flexibility than the valve post 1112.

The valve 101 includes at least three flexible leaflets 1130 each having a free edge 1132, an attached edge 1133 and a belly 1134. The attached edge 1133 attaches to the outer portion 1110 to form an attachment curve running along the inner diameter of the outer portion between a pair of valve posts 1112. The free edge 1132 defines a free edge curve which extends from a first valve post tip 1120, towards the central axis 1116 and back to second valve post tip 1120. The free edges 1132 of adjacent leaflets 1130 define commissures 1135 at each of the valve post tips 1120. In some embodiments, the free edges 1132 curve upward in the region of the commissures 1135, such that the leaflets 1130 have a horned shape in the region around each of the valve post tips 1120, as shown.

The outer portion 1110 of the valve body may be attached to the mounting ring 206. For example, in some embodiments, the material of the valve body may adhere to and/or encapsulate all or a portion of the ring 206.

Each of the valve posts 1112 may be attached to a respective one of the elongated posts 205 of the stent 102 (not shown). For example, in some embodiments, the material of the valve post 1112 may adhere to and/or encapsulate all or a portion of the post 205, e.g., as shown in FIG. 4. In some embodiments, the posts 205 may include one or more features that facilitate connection to the valve posts 1112. For example, as shown in FIGS. 2A-4, the posts 205 may include holes that allow the material of the valve posts 1112 to extend through and around the post 205, to provide a stronger connection.

In operation, when blood flows in the forward direction, i.e., towards the top of the figure, the pressure of the blood flow causes the leaflets 1130 to deflect away from a central axis 1116 of the valve body 1101. In this "open" position, the leaflets 1130 define a large flow orifice (not shown) allowing the blood to flow freely in the forward direction. With the leaflets 1130 in the open position, the valve 101 presents little resistance to fluid flow. When blood flows in the reverse direction, i.e., towards the bottom of the figure, the pressure of the blood flow causes the valve post tips 1120 and the leaflets 1130 to deflect toward the central axis 1116. In this "closed" position, the leaflets 130 engage each other along the free edges 132, which help the valve 101 seal against reverse flow.

As shown, the leaflets 1130 are cast in a partially open position at rest (i.e. in the absence of forward or reverse fluid pressure against the valve). For example, in some embodiments the at rest opening of commissures in the region closest to their respective flexible valve post tip 1120 is in the range of 0.60 mm or less, e.g. about 0.25 mm.

For example, the open area of the valve 101 in the at-rest position (e.g., the open cross sectional area presented to fluid flow through the valve) may be a suitable fraction of the open area of the valve in the absence of the leaflets 1130. In some embodiments the open area in the partially open at rest positions may be greater than 5%, 10%, 25% or more of the open area, e.g., in the range of 5-10%, 10-20%, 10-30%, or any other suitable range.

This configuration reduces the energy required to open the leaflets during forward blood flow relative to that required for opening an equivalent valve formed in a closed position at rest. The relative ease of opening of valve 101 when formed in the partially open rest position results in a decrease in forward flow pressure loss.

Furthermore, the partially open rest position leaflet geometry helps ensure a symmetric opening of the leaflets 1130 in response to forward flow, even in cases where the flow is not uniformly distributed (e.g. due to the specifics of the heart anatomy, or other factors). For example, by providing the leaflets 1130 in the partially open rest configuration, the valve can avoid unwanted adhesion of free edges of one or more pairs of adjacent leaflets 1130 to one another. This prevents low fluid velocities in the commissure 1135 between the leaflets 1130.

Moreover, this valve structure can reduce or prevent the occurrence a "lazy leaflet", i.e., a leaflet that does not properly and completely move between its intended open and closes positions.

Avoiding low fluid flow and/or asymmetric flow patterns allows the valve to be properly washed through by the flow of blood in both forward and reverse directions, reducing or eliminating the build up of unwanted materials in the valve. This can lead to a reduction or even elimination of deleterious effects, e.g., thrombosis.

When transitioning from the partially open rest position to the closed position, the valve posts 1112 flex inward toward the central axis to allow leaflets 1130 to close properly to seal the valve against reverse flow. This flexing beneficially reduces strain on the leaflets 1130, reducing or eliminating the occurrence of tears, and improving the reliability and durability of the valve 101. Moreover, in some embodiments, the tips 1120 of valve posts are formed of a material that is more flexible than the remainder of the valve posts 1112. This allows for increased flexing in the area near the commissures 1135 without compromising the overall structural integrity of posts 1112. Accordingly, force may be transferred from the leaflets 1130 to the valve posts 1112 through tips 1120 while reducing or eliminating unwanted stress concentrations in the leaflets 1130. In other words, the flexible post tips 1120 serve as a strain relief for the leaflet 1130 transition to the valve posts 1112 while reducing stress concentrations in the leaflets 1130 thereby increasing reliability of the polymeric valve 101. Note also that, due to the transition from stiff to soft material in the post tips 1120, relatively short, low profile posts 1112 may be used.

In some embodiments, each flexible valve post tip 1120 extends beyond the free edge 1132 of the leaflets 1130 where the leaflets attach to the posts 1112 (i.e. near commissures 1135). In some embodiments, each flexible tip 1120 extends beyond the free edge of the leaflets by 1 mm to 2 mm, e.g., by 1.5 mm. In some embodiments, this flexible tip configuration acts to reduces stress concentrations between the softer leaflet 1130 material and the harder post 1112 in order to increase the valve reliability. Although not shown, in some embodiments, the posts 205 of the stent 102 extends through the valve posts 1112, and out through the tips 1120.

In some embodiments, a portion of the free edge 1132 of the leaflet 1130 is substantially straight, extending radially towards the central axis 1116. As noted above, in one embodiment, portions of the free edge 1132 of the leaflet 1130 curve upward slightly at the valve post tip 1120. In one embodiment, the belly 1134 of the leaflet 1130 has a thickness profile less than a thickness profile of the free edge 1132 of the leaflet 1130. The thickness profile of the free edge 1132 can be in the range of 1 to 2.5 times greater than the thickness profile of the belly 1134. The leaflets can be made from a biocompatible polymer, such as silicone and/or polyurethane.

In various embodiments any other suitable valve may be used for valve 101 including any suitable polymeric valve known in the art.

In various embodiments any suitable dimensions for the device 100 may be used. For example, in some embodiments, the device 100 has an outer diameter of about 23 mm or about 27 mm. In some embodiments, the device 100 has an outer diameter in the range of 10-100 mm, or any subrange thereof. In some embodiments, the device has a total length of about 48 mm. In some embodiments, the device has a total length of in the range of 10-100 mm, or any subrange thereof. In some embodiments, the wall thickness of the tubular stent 102 is about 0.5 mm. In some embodiments, the wall thickness of the tubular stent 102 is about 0.1-1.0 mm or any subrange thereof.

Figure 6:
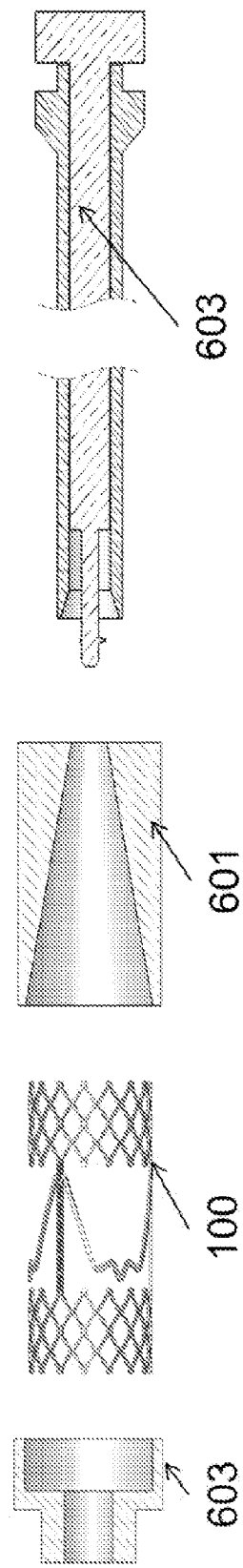
FIG. 6 is an illustration of a kit for crimping the prosthetic device of FIG. 4 onto a introducer.

In some embodiments, the device 100 may be crimped to reduce its outer diameter to allow for percutaneous implantation, e.g., using transcatheter techniques known in the art. For example, FIG. 6 illustrates a kit used for crimping the device 100. The kit includes a cone 601, a cap 602, and an introducer sleeve 603. The device 100 is inserted into the wide end of the cone 601 and capped with the cap 602. The introducer sleeve 603 is attached to the device 100 (e.g. using one or more pins which attach to the stent 102). The cone 601 is pushed back while the sleeve 603 is advanced. The device 100 is crimped as it passes out through the narrow end of the cone and is inserted within the sleeve 100.

In various embodiments, the device 100 may be crimped to any suitable size. In some embodiments, e.g., where the device 100 has an outer diameter in the range of 20-30 mm, the device may be crimped to a reduced outer diameter in the range of 4-10 mm, e.g., to a sufficiently small outer diameter for use with a catheter introduction system with a catheter size in the range of 12-30 Fr (in the familiar French catheter size scale). Advantageously, in some embodiments, positioning of the open regions 207 adjacent the leaflets of the valve 101 allows the device to be crimped down to a small size without damaging the sensitive valve leaflets.

Figure 7:
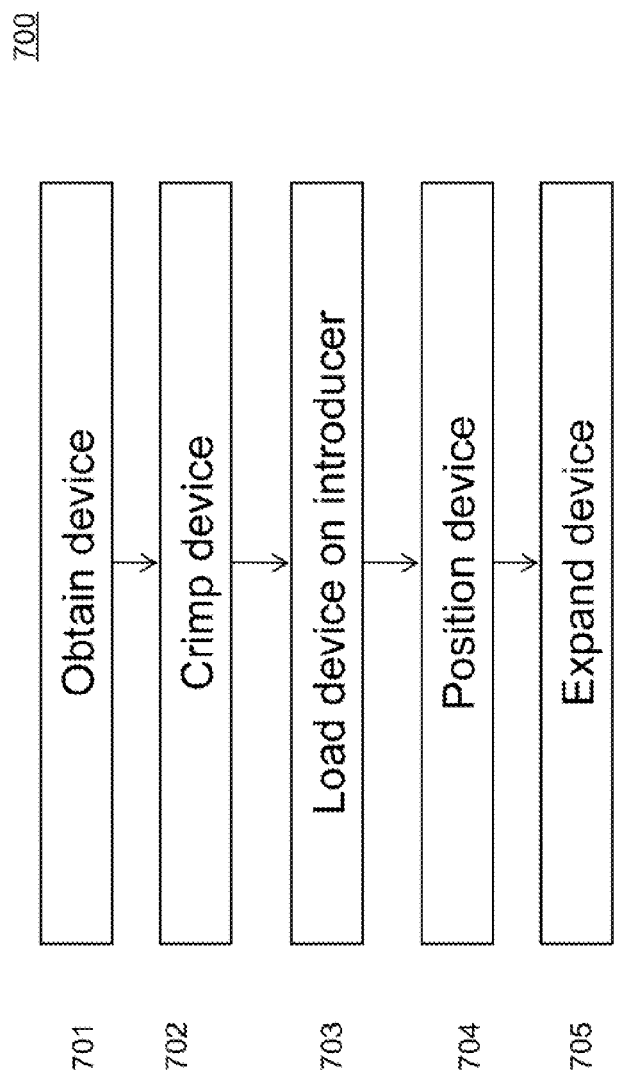
FIG. 7 is a flow chart illustrating the steps for implanting a prosthetic device.

FIG. 7 is a flow diagram 700 illustrating the steps for implantation of the device 100. In step 701, the device is obtained. In step 702 the device is crimped to reduce its outer diameter. In step 703 the device is loaded on to an introducer (e.g. as described with reference to FIG. 6). In step 704 the device is positioned at a desired location in a subject, e.g., using a transcatheter method. In step, 705 the device is expanded back to its uncrimped size, e.g., by removing the introducer. In some embodiments the device 100 is self expanding (e.g., owing to shape memory properties of the stent 102). In some embodiments an expander, such as a balloon catheter expander may be used.

Figure 8:
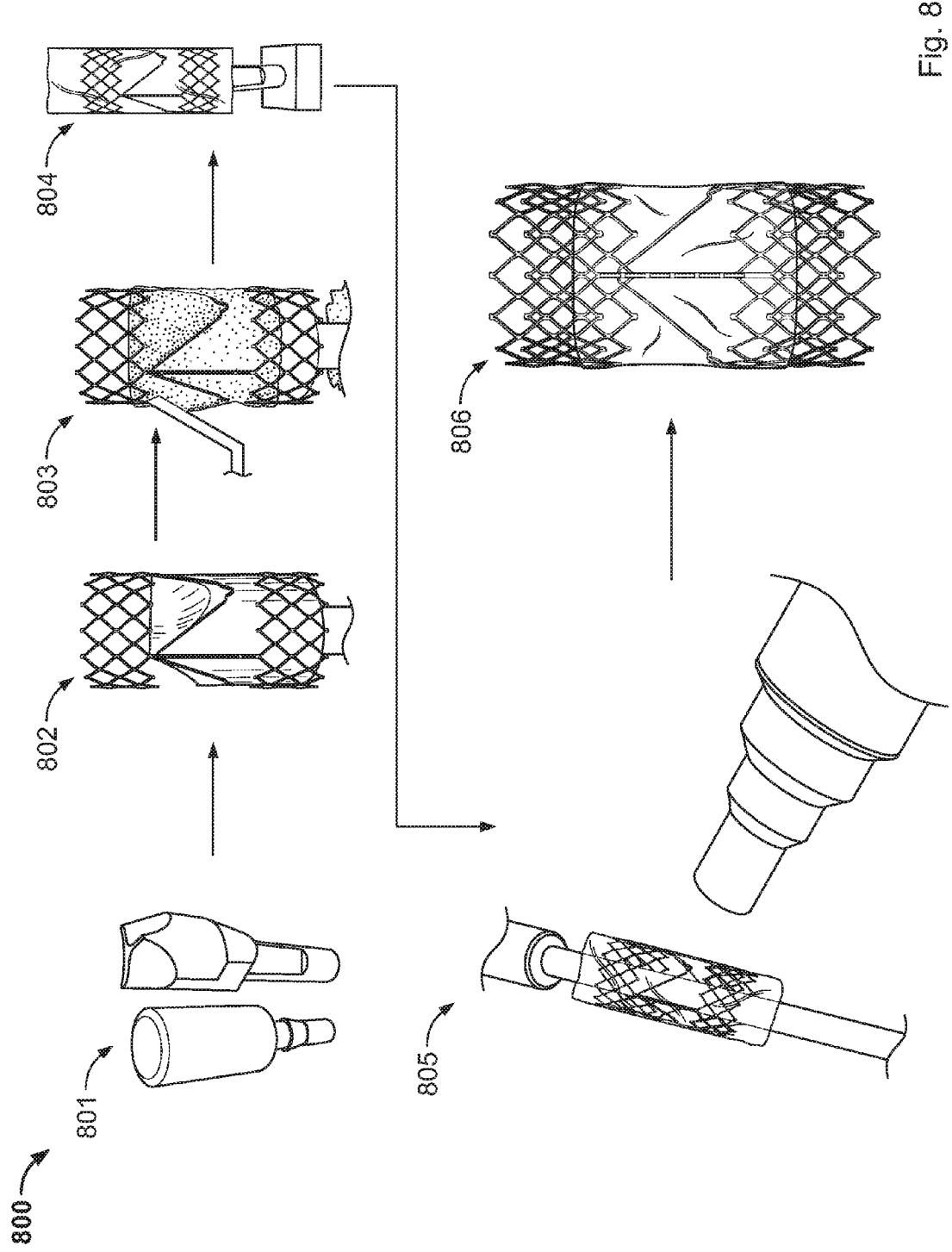
FIG. 8 is an illustration of a method of making the prosthetic device of FIG. 4.

FIG. 8 illustrates a method 800 of making the device 100 shown in FIG. 4. In step 801, a mandrel is obtained having a portion with a shape corresponding to the shape of the valve 101. In step 802, the stent 102 is obtained and placed over the mandrel. The stent may be constructed using any suitable technique know in the art including molding, welding, brazing, etc.

In step 803, the valve 101 is formed on the mandrel, e.g., using a dip molding process of the type described in the Valve Application , incorporated by reference above.

For example, in some embodiments, the mandrel and the stent 102 may be cleaned with alcohol. Next, a polymer conduit is placed on the valve mandrel and the stent 102. Optionally, strips of flexible material (e.g., a polymer such as Angioflex) may be adhered the posts 205 of the stent 102 to form the to reinforce this area. The mandrel assembly is dipped in a polymer solution having a suitable viscosity, e.g., within the 730±50 cp range. In some embodiments, the polymer solution can be an Angioflex solution produced by Abiomed of Danvers, Mass. At this step, the valve mandrel is cleaned, e.g. with alcohol. Next, the valve mandrel is placed upside down in a container of Dioxane, e.g., for 30 seconds so that the entire stent is covered. Next, the valve mandrel is dipped in the polymer solution. Once the valve mandrel is removed from the solution any excess solution is removed. The dipping process may be repeated to obtain a desired leaflet profile.

Although one valve fabrication process has been described above, it is to be understood that any suitable fabrication technique know in the art may be employed. For example, the valve 101 may be fabricated using one or more of the techniques described in Labma N M K, Woodhouse K A, Cooper S L. *Polyurethanes in Biomedical Applications.* 1998 CRC Press LLC, Boca Raton, Fla., p. 33.; Lyman D J, Searl W J, Albo D, Bergman S, Lamb J, Metcalf L C, and Richards K. Polyurethane elastomers in surgery. *Int J Polym Mater,* 5:211, 1977; Boretos J W. *Procedures for the fabrication of segmented polyurethane polymers into useful biomedical prostheses.* National Institutes of Health, 1968.; snf Kardos J L, Mehta B S, Apostolou S F, Thies C, and Clark R E. Design, fabrication and testing of prosthetic blood vessels. *Biomater Med Dev Artif Organs,* 2:387, 1974.

In step 804, after molding the valve, a heat shrink tube is placed over the conduit and stent 102 on the mandrel. The heat shrink tubing may be made of a thermoplastic material such as polyolefin, fluoropolymer (such as fluorinated ethylene propylene, polytetrafluoroethylene or polyvinylidene fluoride), polyvinyl chloride, neoprene, silicone elastomer, Viton, etc.

In step 805, heat is applied, e.g., with a heat gun, to soften the conduit and cause the heat shrink tubing to contract around the mandrel. The contracting tubing applies a force which molds the softened material of the conduit, e.g., causing it to flow around and encapsulate at least a portion of the stent 102 to form the sheath 300. This molding process may be referred to as "thermoforming". In some embodiments, the valve 101 is cooled during the thermoforming process (e.g., by application of an air flow), to avoid thermal damage to the valve 101.

After cooling, the heat shrink tubing is removed (e.g. cut and peeled away). The valve 101 may be cut (e.g., using laser cutting) to free the valve leaflets.

In step 806, the assembly is removed from the mandrel, resulting in the device 100 as shown in FIG. 4. Some embodiments include an additional step (not shown) of securing the sheath 300 to the stent 102 using, e.g. sutures.

In some embodiments, the valve 101 is formed in the partially open position as described above, and may exhibit advantageous hemodynamic performance FIG. 9 shows a table detailing forward pressure loss as a function of flow rate for embodiments of the valve 101 with various leaflet thicknesses. The pressure loss increases roughly linearly as a function of flow rate, from a loss of about 6-7 mmHg at a flow rate of 5 L/minute to a loss of about 22-25 mmHg at a flow rate of 25 L/minute. Other embodiments may exhibit even lower pressure drops, e.g., reduced by a factor of two or more from the values shown. For example, some embodiments may have a pressure drop of about 5 mmHg or less at a flow rate of 10 L/minute.

In some embodiments, this performance is comparable or superior to that of a comparable bioprosthetic valve or a comparable mechanical valve. Some embodiments feature the utilization of flexible and peripherally located leaflets which avoid blood flow disturbances such as cavitation and stagnation leading to cell damage and thrombosis. Additional performance benefits include the avoidance of reliability issues typically associated with bioprosthesis (i.e., problems with limited life from structural changes such as calcification and leaflet wear, leading to valve failure— biological tissue fixation and methods used to mount the tissue to a supporting stent may account for this shortcoming).

FIG. 10 shows a plot of valve leakage detailing forward pressure loss as a function of flow rate for embodiments of the valve 101 with various leaflet thicknesses. The valve leakage rate at a reverse flow pressure of 85 mmHg is less than about 8 mL/second in some embodiments, and less than about 4 mL/second in another embodiment. Further embodiments may have even lower leakage rates. This performance is comparable or superior to that of a comparable mechanical valve or bioprosthesis valve.

The closing volume loss of for embodiments of the valve 101 may be, e.g., less than about 10 mL, 8 mL 6, mL, 4 mL, 2 mL, 1 mL, or less. (e.g., corresponding to a hydraulic efficiency of at least 80%, at least 85%, or more). This performance is comparable or superior to that of a comparable mechanical valve or bioprosthesis valve.

The embodiments disclosed herein are to be considered in all respects as illustrative, and not restrictive of the invention. The technology described herein is in no way limited to the embodiments described above. Various modifications and changes may be made to the embodiments without departing from the spirit and scope of the invention. The scope of the invention is indicated by the attached claims, rather than the embodiments. Various modifications and changes that come within the meaning and range of equivalency of the claims are intended to be within the scope of the invention.

Although a number of examples of devices for aortic valve replacement have been given, it is to be understood that the devices and techniques described herein may be applied to other applications, including the replacement of other heart valves.

Although examples of devices for use with adult human subjects have been described, it is to be understood that, in some embodiments, the devices and techniques may be used to treat infant, juvenile or adult human or animal subjects.

While various inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

The above-described embodiments can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Also, various inventive concepts may be embodied as one or more methods, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of" and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

What is claimed is:

1. A prosthetic apparatus comprising:
   a tubular stent disposed about a longitudinal axis and extending from a proximal end to a distal end, the tubular stent defining a tubular passage between the ends, wherein:
   the tubular stent has a proximal portion, a distal portion, and a middle portion located between the proximal and distal portions;
   the proximal and distal portions each comprise a mesh of support struts forming at least one ring of open elements disposed about the longitudinal axis; and
   the middle portion comprises:
      a plurality of elongated posts extending along a direction substantially parallel the longitudinal axis between the proximal and distal portions;
      a crown shaped mounting ring attached to the posts and configured to mount a polymeric valve within the tubular passage; and
      a plurality of open regions; and
   a tubular polymeric sheath extending along the outer surface of each support strut from the proximal portion to the distal portion, wherein the tubular polymeric sheath does not substantially cover the plurality of open regions in the middle portion.

2. The apparatus of claim 1, wherein the open elements are open diamond shaped elements.

3. The apparatus of claim 2, wherein the plurality of open regions each define an open area along the outer surface of each support strut that is at least about 20 times the area of each of the open elements.

4. The apparatus of claim 3, wherein the plurality of open regions each define an open area along the outer surface of each support strut that is at least about 40 times the area of each of the open elements.

5. The apparatus of claim 3, wherein each of the proximal and distal portions comprise a ring of open elements, the plurality of elongated posts consist of posts extending between the rings, and the ratio of the number of open elements in each of the rings to the number of posts extending between the rings is at least 4 to 1.

6. The apparatus of claim 5, wherein the ratio of the number of open elements in each of the rings to the number of posts extending between the rings is at least 5 to 1.

7. The apparatus of claim 5, wherein the ratio of the number of open elements in each of the rings to the number of posts extending between the rings is at least 6 to 1.

8. The apparatus of claim 6, wherein the number of open elements in each of the rings is 15 and the number of posts extending between the rings is 3.

9. The apparatus of claim 1, wherein the sheath encapsulates the elongated posts.

10. The apparatus of claim 9, wherein the sheath comprises regions of reinforced thickness corresponding to the elongated posts.

11. The apparatus of claim 9, wherein the sheath comprises regions of reinforced thickness corresponding to one or more of the support struts or the mounting ring.

12. The apparatus of claim 1, further comprising one or more sutures securing the sleeve to the stent.

13. The apparatus of claim 1, further comprising the polymeric heart valve, wherein the valve comprises:
   a valve body having a central axis extending along the direction of the longitudinal axis of the tubular stent and having a body fluid pathway extending along the central axis from an inflow end to an outflow end;

a flexible outer support disposed about an outer circumference of the body and comprising at least three flexible valve posts each extending in the axial direction to a tip and each attached to at least one of the elongated posts; and at least three flexible leaflets extending from the crown shaped mounting ring, each of the leaflets having an attached edge defining an attachment curve along the mounting ring extending between a respective pair of flexible valve posts, and wherein pairs of leaflets define a respective commissure at each of the at least three flexible valve posts;

wherein the crown shape ring comprises a plurality of points each corresponding to a flexible valve post and attached to a respective one of the elongated posts of the stent.

14. The apparatus of claim 13, wherein:

the at least three leaflets define a partially open position at rest, a fully open position deflecting away from the central axis during forward blood flow along a direction from the inflow end to the outflow end, and a closed position deflecting toward the central axis during reverse blood flow along a direction from the outflow end to the inflow end, and in the closed position, each of the flexible valve posts flexes inward toward the central axis.

15. The apparatus of claim 14, wherein the tip of each valve post is formed of a material having a flexibility greater than the remainder of the valve post.

16. The apparatus of claim 15, wherein the stent is configured to be crimped to reduce the outer diameter of the stent from an uncrimped diameter to a crimped diameter without damaging the valve.

17. The apparatus of claim 16, wherein the uncrimped diameter is at least about 20 mm and the crimped diameter is less than about 6 mm.

18. The apparatus of claim 1, wherein the tubular stent comprises a shape memory material.

19. The apparatus of claim 18, wherein the shape memory material comprises Nitinol.

20. The apparatus of claim 1, wherein the stent is a self expanding stent.

21. The apparatus of claim 1, wherein the stent is configured such that, when implanted in the human heart such that the valve is positioned proximal a location of a native aortic valve, the open regions are positioned proximal to the coronary ostia.

22. The apparatus of claim 1, wherein the apparatus consists essentially of biocompatible materials.

23. A method comprising;

obtaining the apparatus of claim 1; and percutaneously implanting the apparatus in a human subject such that that the valve is positioned proximal a location of a native aortic valve, the open regions are positioned proximal to the coronary ostia.

24. The method of claim 23, wherein the step of percutaneously implanting the apparatus comprises:

crimping the stent;

using an introducer to position the stent in a desired location; and removing the introducer and expanding the stent to an uncrimped state.

25. The method of claim 24, wherein expanding the stent to an uncrimped state comprises allowing the stent to self expand.

26. A method of making prosthetic apparatus comprising:

obtaining a tubular stent disposed about a longitudinal axis and extending from a proximal end to a distal end, the stent defining a tubular passage between the ends;

wherein the tubular stent has a proximal portion, a distal portion, and a middle portion located between the proximal and distal portions;

wherein the proximal and distal portions each comprise a mesh of support struts forming at least one ring of open elements disposed about the longitudinal axis;

wherein the middle portion comprises:

a plurality of elongated posts extending along a direction substantially parallel the longitudinal axis between the proximal and distal portions; and a crown shaped mounting ring attached to the posts and configured to mount a polymeric valve within the tubular passage; and a plurality of open regions;

placing the stent on a mandrel;

forming a polymeric valve mounted on the mounting ring by a process comprising dip molding; and forming a tubular polymeric sheath extending along the outer surface of each support strut from the proximal portion to the distal portion, but does not substantially cover the open regions in the middle portion.

27. The method of claim 26, wherein the step of forming the tubular polymeric sheath includes a thermoforming process comprising:

applying a polymer material to the outer surface of the tubular stent;

disposing a heat shrink tube about the polymer material and the stent; and applying heat to soften the polymer material and cause the heat shrink tube to shrink and apply force to mold the polymer material to form the sheath.

28. The method of claim 27, wherein forming the sheath comprises encapsulating one or more of the support struts and the elongated posts.

29. The method of claim 27, further comprising, during the thermoforming process, applying an air flow to valve to avoid thermal damage to the valve.

30. The method of claim 26, further comprising:

applying strips of polymer material to reinforce the sheath at locations corresponding to the elongated posts or the mounting ring.

31. The method of claim 26, further comprising:

applying additional polymer material to reinforce the sheath at locations corresponding to the struts.

* * * * *